(12) United States Patent
Sohn et al.

(10) Patent No.: US 9,099,221 B2
(45) Date of Patent: Aug. 4, 2015

(54) MONOMER FOR BINDING NANO-METAL, CONDUCTIVE POLYMER COMPOSITE AND METHOD OF PREPARING THE CONDUCTIVE POLYMER COMPOSITE

(75) Inventors: Byung Hee Sohn, Yongin-si (KR); Young Kwan Lee, Seoul (KR); Yi Yoiung Yun, Seoul (KR); Won Jae Joo, Seongnam-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 2022 days.

(21) Appl. No.: 12/275,745

(22) Filed: Nov. 21, 2008

(65) Prior Publication Data

US 2009/0286082 A1 Nov. 19, 2009

(30) Foreign Application Priority Data

May 14, 2008 (KR) ........................ 10-2008-0044482

(51) Int. Cl.
*D02G 3/00* (2006.01)
*B05D 3/02* (2006.01)
*H01B 1/22* (2006.01)

(52) U.S. Cl.
CPC ............... *H01B 1/22* (2013.01); *Y10T 428/294* (2015.01)

(58) Field of Classification Search
USPC ......................................................... 549/27
See application file for complete search history.

(56) References Cited

U.S. PATENT DOCUMENTS

| 5,891,968 | A | * | 4/1999 | Wudl et al. | 525/417 |
|---|---|---|---|---|---|
| 5,973,050 | A | * | 10/1999 | Johnson et al. | 524/439 |
| 6,242,561 | B1 | * | 6/2001 | Mohwald et al. | 528/377 |
| 6,331,356 | B1 | | 12/2001 | Angelopoulos et al. | |
| 7,217,295 | B2 | * | 5/2007 | Samain et al. | 8/405 |
| 7,858,181 | B2 | * | 12/2010 | Hanrath et al. | 428/364 |
| 8,269,100 | B2 | * | 9/2012 | Darling et al. | 136/263 |
| 2004/0065970 | A1 | | 4/2004 | Blanchet-Fincher | |
| 2005/0230668 | A1 | | 10/2005 | Lee et al. | |
| 2007/0128762 | A1 | * | 6/2007 | Aizenberg et al. | 438/99 |
| 2009/0286082 | A1 | * | 11/2009 | Sohn et al. | 428/379 |
| 2010/0126981 | A1 | * | 5/2010 | Heintz et al. | 219/482 |
| 2011/0186956 | A1 | * | 8/2011 | Hiroshige et al. | 257/467 |

FOREIGN PATENT DOCUMENTS

JP 2007051319 3/2007
KR 1020070083110 A 8/2007

OTHER PUBLICATIONS

JP2007-051319, Mar. 2007; machine translation.*

* cited by examiner

*Primary Examiner* — Jill Gray
(74) *Attorney, Agent, or Firm* — Cantor Colburn LLP

(57) ABSTRACT

A monomer for binding nano-metal, which is useful for the preparation of a conductor having increased conductivity with ensuring flexibility and transparency. Polymerization of the monomer for binding nano-metal provides a conductive polymer composite including a nano-metal rod. A method of preparing the conductive polymer composite is also provided.

14 Claims, 3 Drawing Sheets

MONOMER FOR BINDING NANO-METAL, CONDUCTIVE POLYMER COMPOSITE AND METHOD OF PREPARING THE CONDUCTIVE POLYMER COMPOSITE

This non-provisional application claims priority to Korean Patent Application No. 10-2008-0044482, filed on May 24, 2008, and all the benefits accruing therefrom under U.S.C. §119, the contents of which are incorporated herein by reference in their entirety.

BACKGROUND

1. Field

This disclosure is directed to a monomer for binding nano-metal, a conductive polymer composite and a method of preparing the conductive polymer composite, and more particularly, to a monomer for binding nano-metal for use in the preparation of a conductive polymer composite including a nano-metal rod, to a conductive polymer composite, and to a method of preparing the conductive polymer composite.

2. Description of the Related Art

Conductive polymers generally have a π-conjugated structure, where such conductive polymers exhibit the properties of a conductor due to delocalization of electron density within the polymer chain from doping to create a delocalizable charge (positive or negative), where the presence of delocalized charge increases electrical conductivity. Doped conductive polymers may have metallic properties, making it possible to use them as agents for blocking (absorbing) electromagnetic waves, as antistatic agents, and as electrodes.

Compared to inorganic semiconductors, such as those based on silicon, electronic devices which use polymers are advantageous in that the fabrication process is very simple, the fabrication cost is low, and various substrates, including different kinds of plastics, can be used. Further, because the electronic energy structure and energy band gap of polymer semiconductors may be readily adjusted by molecular design and control of polymer properties, the use of polymer semiconductors as novel materials is desirable.

Conductive polymers advantageously are mechanically flexible and are capable of being printed upon by a printing process, which is desirable. Where conductive polymers are doped in order to impart electrical conductivity, drawbacks such as decreased polymer solubility and light transmittance may occur. And, while the solubility of conductive polymers may be increased, electrical conductivity tends to decrease relative to similar polymer materials that are unmodified.

SUMMARY

Accordingly, there is a continuous need for the development of conductive polymers which can ensure not only high electrical conductivity but also high solubility and light transmittance.

Disclosed herein is, in an embodiment, a monomer for binding nano-metal, for the preparation of a conductive polymer composite having high conductivity while ensuring transparency and flexibility.

Also disclosed herein is, in an embodiment, a conductive polymer composite having high conductivity while ensuring transparency and flexibility.

Also disclosed herein is, in an embodiment, a method of preparing the conductive polymer composite.

In a specific embodiment, a monomer for binding nano-metal, represented by Formula 1 below, is provided:

$$Ar-L_1-A \qquad \text{[Formula 1]}$$

wherein Ar is a thiophenyl, anilinyl, pyrrolyl, furanyl, pyrazolyl, carbazolyl, fluorenyl or a derivative thereof, $L_1$ is a $C_{1\sim10}$ alkylene group containing one or more heteroatoms selected from the group consisting of S, O, N and Si; a $C_{1\sim10}$ alkyleneoxy group containing one or more hetero atoms selected from the group consisting of S, O and N; or a $C_{1\sim10}$ silyleneoxy group containing one or more hetero atoms selected from the group consisting of S, O and N; and A is —SH, —COOH, —SOOH, —CN, —CH$_2$=CH$_2$, —C≡CH, —NH$_2$, or trichlorosilyl.

In another specific embodiment, a conductive polymer composite including a nano-metal rod is provided, wherein the surface of the nano-metal rod is bound with the monomer for binding nano-metal, as represented by Formula 1, and to which conjugated conductive polymer monomers are joined.

In a further specific embodiment, a method of preparing the conductive polymer composite is provided, the method including (a) binding the monomer for binding nano-metal, as represented by Formula 1, to the surface of a nano-metal rod, thus forming a nano-metal-bound monomer; and (b) mixing the nano-metal-bound monomer formed in (a), a conductive polymer monomer, a polymerization initiator, and a dopant with a solvent, to obtain a mixture, and then subjecting the mixture to heating and polymerization.

BRIEF DESCRIPTION OF THE DRAWINGS

The exemplary embodiments will be more clearly understood from the following detailed description taken in conjunction with the accompanying drawings, in which.

DETAILED DESCRIPTION

Figure 1:
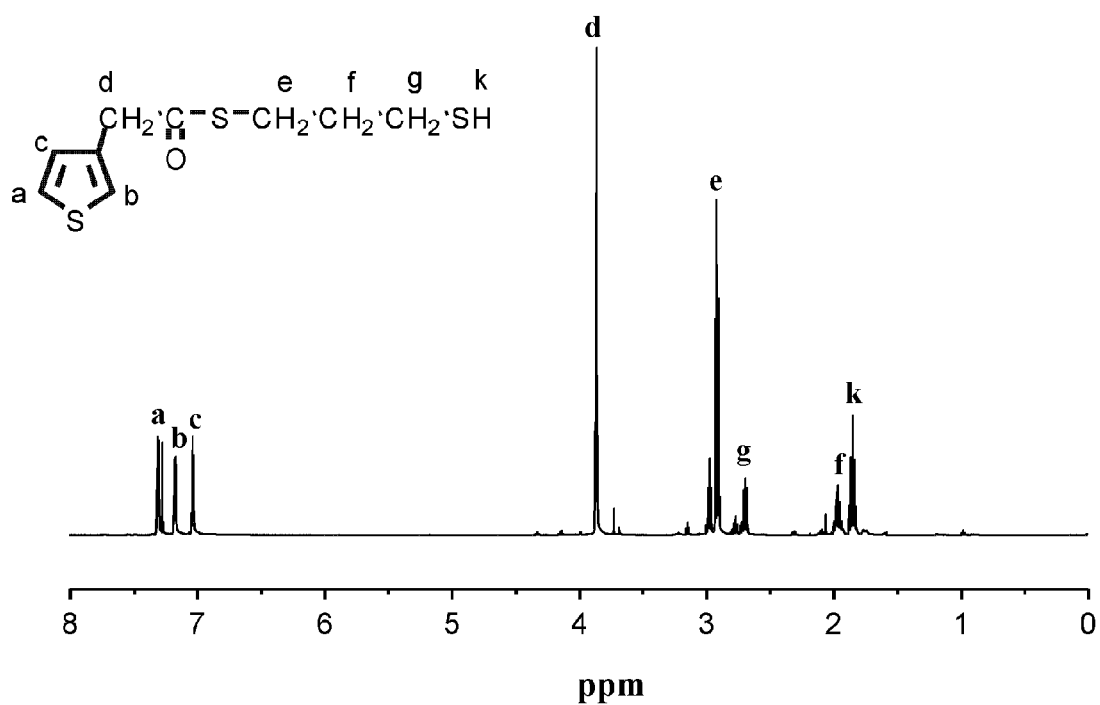
FIG. 1 is an H$^1$-NMR spectrum of an exemplary monomer for binding nano-metal, synthesized in the Example.

Hereinafter, a detailed description of a monomer for binding nano-metal, a conductive polymer composite, and a method of preparing the conductive polymer composite are provided according to exemplary embodiments.

In an embodiment, a novel monomer for binding nano-metal is provided. The monomer for binding nano-metal may be used for the preparation of a conductive polymer composite including a nano-metal rod.

The monomer for binding nano-metal is represented by Formula 1 below.

$$Ar-L_1-A \qquad \text{[Formula 1]}$$

wherein Ar is thiophenyl, anilinyl, pyrrolyl, furanyl, pyrazolyl, carbazolyl, fluorenyl or derivatives thereof, $L_1$ is a $C_{1\sim10}$ alkylene group containing one or more heteroatoms selected from the group consisting of S, O, N and Si; a $C_{1\sim10}$ alkyleneoxy group containing one or more hetero atoms selected from the group consisting of S, O and N; or a $C_{1\sim10}$ silyleneoxy group containing one or more heteroatoms selected from the group consisting of S, O and N; and A is —SH, —COOH, —SOOH, —CN, —CH$_2$=CH$_2$, —C≡CH, —NH$_2$, or trichlorosilyl.

Examples of the monomer for binding nano-metal, as represented by Formula 1, include, but are not limited to, monomers for binding nano-metal represented by Formulas 2 to 6 below.

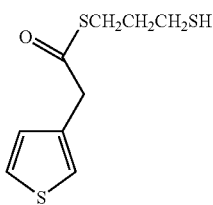
[Formula 2]

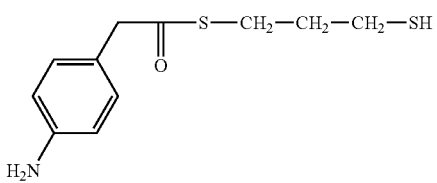
[Formula 3]

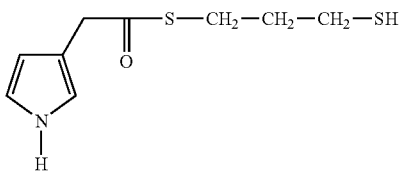
[Formula 4]

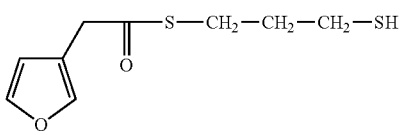
[Formula 5]

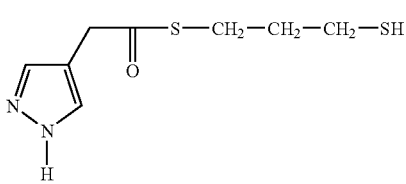
[Formula 6]

The monomer for binding nano-metal, represented by Formula 1, may be prepared by dissolving as reaction starting materials a first reactive compound comprising thiophenyl, anilinyl, pyrrolyl, furanyl, pyrazolyl, carbazolyl, fluorenyl or derivatives thereof; a second reactive compound comprising a $C_{1~10}$ alkylene group, a $C_{1~10}$ alkyleneoxy group or a $C_{1~10}$ silyleneoxy group, containing one or more hetero atoms with —SH, —COOH, —SOOH, —CN, —CH$_2$═CH$_2$, —C≡CH, —NH$_2$, or trichlorosilyl; and n,n'-dimethyl-4-aminopyridine ("4-DMAP") as a catalyst in a solvent, mixing them at 0 to 100° C. under a nitrogen atmosphere, adding a reagent (such as, for example, a dehydrating agent), reacting the mixture for 4 to 16 hours, filtering the resulting reaction solution, washing the reaction solution, drying to remove the remaining solvent to afford a crude product, repeatedly performing precipitation and solvent washing of the crude product, and performing purification of the precipitated, partially purified product by crystallization, chromatography, sublimation, or other method, and thereby obtaining a pure monomer material.

In another embodiment, a conductive polymer composite using the monomer for binding nano-metal mentioned above is provided.

The conductive polymer composite includes a nano-metal rod, wherein the surface of the nano-metal rod has bound to it the monomer for binding nano-metal, to which conjugated conductive polymer monomers are joined.

The conductive polymer composite is prepared by attaching the monomer for binding nano-metal to the nano-metal rod to thus form a nano-metal-bound monomer, mixing the nano-metal-bound monomer with a conductive polymer monomer, and then polymerizing the mixture.

The conductive polymer composite including the nano-metal rod, thereby has much higher electrical conductivity than typical conductive polymers, and further, has transparency and flexibility properties comparable to those of conductive polymers, and is thus capable of being used for flexible devices. Also, a device may be fabricated through a printing process, as an example of a solution process, thereby conveying process advantages. Furthermore, because the conductive polymer composite is transparent, it is capable of being utilized in various displays.

The polymer moiety of the conductive polymer composite has a conjugated structure of alternating single and double carbon-carbon bonds to provide a delocalized π-electron structure. Accordingly, when the energy band gap of the conductive polymer composite is decreased with the use of a dopant, electrical charges are allowed to move in the conductive polymer. Further, because the conductive polymer composite includes the nano-metal rod, electrical conductivity can be further increased compared to when only a conductive polymer is used.

Further, —SH, —COOH, —SOOH, —CN, —CH$_2$═CH$_2$, —C≡CH, or trichlorosilyl, located at an end of the monomer of Formula 1, is bound to the surface of the nano-metal rod.

The nano-metal is conductive metal, and examples thereof include, but are not limited to, gold (Au), copper (Cu), silver (Ag), platinum (Pt), aluminum (Al), indium (In), tin (Sn), iron (Fe), nickel (Ni), lead (Pb), zinc (Zn), mercury (Hg), palladium (Pd), and alloys thereof.

The nano-metal rod has a diameter of from about 1 nm to about 500 nm and a length of from about 1 μm to about 100 μm. The ratio of diameter to length is from about 1:1 to about $1:10^6$.

Examples of the conductive polymer monomer useful for the polymerization of the conductive polymer composite include 3,4-ethylenedioxythiophene, thiophene, aniline, pyrrole, vinylcarbazole, acetylene, pyridine, azulene, indole, phenylacetylene (to provide phenylenevinylene), 1,4-substituted benzenes (to provide phenylene), 2-methoxy-5-(2'-ethyl)hexyloxy-p-phenylacetylene (to provide the corresponding phenylenevinylene), 2-thiophenylacetylene (to provide 2-thienylenevinylene), azines, quinones, phenylmercaptan (to provide phenylene sulfide), furan, isothianaphthene, and derivatives thereof.

In a further embodiment, a method of preparing the conductive polymer composite is provided. In the preparation method, the monomer for binding nano-metal is attached to the nano-metal rod, thus preparing a nano-metal-bound monomer, after which the nano-metal-bound monomer is polymerized with a conductive polymer monomer, finally obtaining a conductive polymer composite. In the polymerization procedure, a dopant is provided together with the monomers, so that doping is conducted at the same time as polymerization, thus preparing the conductive polymer composite. In this way, the preparation and application of the conductive polymer composite become easier.

Specifically, the method of preparing the conductive polymer composite includes (a) attaching the monomer for binding nano-metal, represented by Formula 1 below, to the surface of the nano-metal rod, thus forming the nano-metal-bound monomer; and (b) mixing the nano-metal-bound monomer formed in (a), the conductive polymer monomer, a polymerization initiator, and a dopant with a solvent, and then performing heating and polymerization.

$$Ar-L_1-A \quad \text{[Formula 1]}$$

wherein Ar is thiophenyl, anilinyl, pyrrolyl, furanyl, pyrazolyl, carbazolyl, fluorenyl or derivatives thereof; $L_1$ is a $C_{1\sim10}$ alkylene group containing one or more hetero atoms selected from the group consisting of S, O, N and Si, a $C_{1\sim10}$ alkyleneoxy group containing one or more hetero atoms selected from the group consisting of S, O and N, or a $C_{1\sim10}$ silyleneoxy group containing one or more hetero atoms selected from the group consisting of S, O and N; and A is —SH, —COOH, —SOOH, —CN, —CH$_2$=CH$_2$, —C≡CH, —NH$_2$, or trichlorosilyl.

In (a), the process of attaching the monomer for binding nano-metal to the nano-metal rod is not particularly limited.

For example, because —SH, —COOH, —SOOH, —CN, —CH$_2$=CH$_2$, —C≡CH, —NH$_2$, or trichlorosilyl, which is located at an end of the monomer for binding nano-metal, as represented by Formula 1, has high bindability with metal, merely by mixing the monomer for binding nano-metal and the nano-metal rod in the solvent, the bond between the nano-metal and the monomer is formed. Examples of the solvent useful in the exemplary embodiments include dimethylformamide ("DMF"), isopropyl alcohol, tetrahydrofuran ("THF"), benzene, toluene, methanol, ethanol, and N-methylpyrrolidone ("NMP"), which may be used alone or in mixtures thereof.

Examples of the monomer for binding nano-metal, represented by Formula 1, which may be used in the preparation method, include, but are not limited to, monomers represented by Formulas 2 to 6 below.

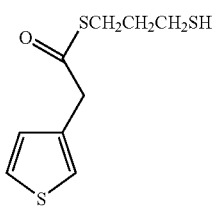

[Formula 2]

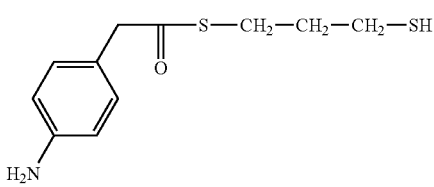

[Formula 3]

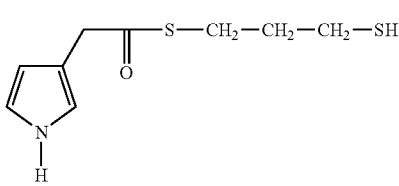

[Formula 4]

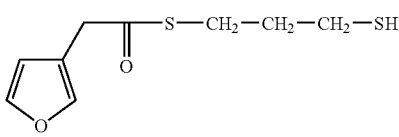

[Formula 5]

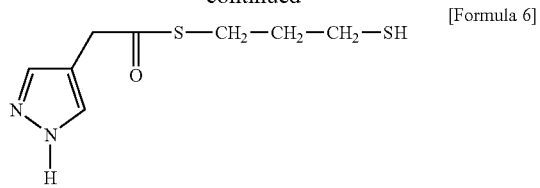

[Formula 6]

The nano-metal used in the preparation method is conductive metal, and examples thereof include, but are not limited to, gold (Au), copper (Cu), silver (Ag), platinum (Pt), aluminum (Al), indium (In), tin (Sn), iron (Fe), nickel (Ni), lead (Pb), zinc (Zn), mercury (Hg), palladium (Pd), and alloys thereof.

Examples of the conductive polymer monomer include, but are not limited to, 3,4-ethylenedioxythiophene, thiophene, aniline, pyrrole, vinylcarbazole, acetylene, pyridine, azulene, indole, phenylacetylene, substituted benzene, azines, quinone, phenylmercaptan, furan, isothianaphthene, and derivatives thereof.

Examples of the polymerization initiator useful in the polymerization procedure include, but are not limited to, ferric (III) p-toluene sulfonate ("FTS"), and ferric (III) chloride (FeCl$_3$). Examples of the dopant include, but are not limited to, p-toluene sulfonic acid, polystyrene sulfonic acid, salts of sulfonic acid and metal, such as lithium polystyrene sulfonate, lithium p-toluene sulfonate, poly(styrene ammonium sulfonate), ammonium p-toluene sulfonate, sodium polystyrene sulfonate, sodium p-toluene sulfonate, poly(styrene potassium sulfonate), and potassium p-toluene sulfonate, and combinations thereof. Any dopant may be used without limitation as long as it is typical in the art. In the case of ferric (III) p-toluene sulfonate (FTS), it functions not only as a polymerization initiator but also as a dopant, thus decreasing the energy band gap of the polymer, thereby imparting conductivity to the polymer.

In (b), the molar ratio of the conductive polymer monomer to the polymerization initiator is from 1:1 to 1:3. The nano-metal rod is added to the conductive polymer monomer solution, stirred, added with a polymerization initiator, and stirred, thereby obtaining a mixture solution, after which the mixture solution is applied on the upper surface of a predetermined substrate, and is then heated and polymerized, thereby obtaining a desired conductive polymer composite. Alternatively, after polymerization, spin coating may be performed. Hence, the process of producing the conductive polymer composite film is not particularly limited, and the form thereof is not necessarily limited to film.

In addition, in (b), a mixture catalyst may be further added. An example of the mixture catalyst is imidazole. In the case where FTS is used as a polymerization initiator, FTS is a strong oxidizer and thus can function to rapidly polymerize the conductive polymer monomer even at room temperature. As such, imidazole plays a role as a polymerization inhibitor for adjusting the polymerization rate in order to ensure transparency.

In accordance with still a further embodiment, a device including the conductive polymer composite is provided. The conductive polymer composite including the nano-metal rod has high conductivity and superior processability, such as flexibility and transparency, and may thus be fabricated in part by a solution process, for ready processability. The conductive polymer composite may be applied to transparent electrodes for various displays, electrodes for solar cells, films for removing static electricity and blocking harmful electromagnetic waves, circuits, cells, electrodes for light sources, electrochromic devices, sensors, films for blocking electromagnetic waves requiring light transmittance, touch panels, wire electrodes, terminal electrodes for transistors, and antennas and chips for Radio Frequency Identification ("RFID") tags. In this way, the conductive polymer composite may substitute for some conventional metal electrodes and may be used as an alternative to ITO electrodes, and may thus be utilized for flexible devices.

In addition, the conductive polymer composite according to the exemplary embodiments is blended with a general polymer and thus may be more variously applied. Typically, conductive polymers have a negligible difference in electrical conductivity when used in an amount higher than a predetermined level. For example, polyaniline doped with a transparent electrode is blended with poly[2-methoxy-5-(2'-ethylhexyloxy)-1,4-phenylene vinylene] ("MEH-PPV") as a light-emitting layer and thus may be used as a flexible light source. The p-type polymer (MEH-PPV) may be blended with the n-type polymer cyano polyphenylene vinylene ("CN-PPV") or doped with a fullerene (e.g., $C_{60}$), and thus may be used as a light-receiving device. Moreover, the conductive polymer composite may be applied to natural color electroluminescent displays using a polymer thin film, channel materials in polymer field effect transistors ("FETs"), polymer secondary cells, having high output and capacity per unit weight, films for preventing the corrosion of metal, accumulators of electricity, nonlinear optical devices, and electronic devices on a molecular scale.

A better understanding of the exemplary embodiments will be described in more detail with reference to the following examples. However, these examples are given merely for the purpose of illustration, and should not to be construed as limiting the scope of the embodiments.

EXAMPLE (A) Synthesis of Monomer for Binding Nano-Metal

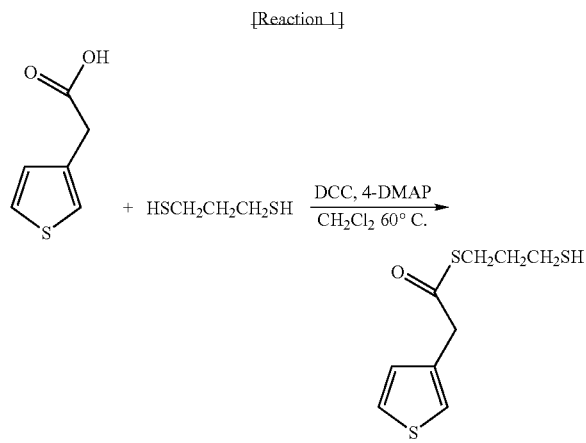

As shown in Reaction 1, 2-(thiophene-3-yl)acetic acid) (1 g, 7.03 mmol), propane-1,3-dithiol (0.753 g, 7.03 mmol), and 4-dimethylaminopyridine (4-DMAP) (2.014 g, 1.75 mol) were dissolved in 80 ml of methylene chloride in a three-neck round bottom flask, after which stirring was performed at 60° C. in a nitrogen atmosphere. The stirred mixture solution was slowly added with N,N'-dicyclohexylcarbodiimide (DCC) (2.89 g, 14.06 mol) dissolved in 20 ml of methylene chloride, and was then allowed to react for 9 hours. The reaction solution was washed using saturated aqueous $Na_2CO_3$, dried over $MgSO_4$, and filtered. The remaining solvent was removed by rotary evaporation to obtain a yellowish solution. This solution was diluted with acetone, and cooled to 0° C., to obtain residual 1,3-dicyclohexylurea ("DCU") as a precipitate. This precipitate was removed by filtration through a paper filter, and addition of acetone and removal of the DCU precipitate were repeated until DCU precipitate was no longer evident in the solution. Finally, the remaining solvent was removed by rotary evaporation, and the crude purified using a silica column eluted with a solution of methylene chloride and methanol (60:1 v/v), thereby producing after collection of the fractions and removal of the solvent, S-3-mercaptopropyl-2-(thiophene-3-yl)ethanethioate ("MTE") (the monomer) as a pure yellow compound. The characteristic $H^1$-NMR spectrum (in acetone-$d_6$) of the product is shown in FIG. 1.

(B) Formation of Nano-Metal Rod (i) Vacuum Evaporation of Copper on Surface of Anodic Aluminum Oxide ("AAO")

Copper was first deposited on a surface of a porous anodic aluminum oxide (AAO) filter. An AAO filter itself is nonconductive, it was necessary to modify a surface of the AAO to be electrically conductive so that electroplating could be performed in the AAO. Thus, using a thermal evaporator system (GVC 2000, available from SNT in Korea), a current of 180 Amperes was applied, and copper was vacuum evaporated on one surface of the AAO for 15 min, thereby providing a conductive AAO.

(ii) Electroplating

After the formation of the Cu/AAO electrode, copper was further electroplated once in AAO using 1 M $CuSO_4$ to provide a surface for a nano-gold rod to be grown, and to create a separation layer. Using PARSTAT 2263 (Princeton Applied Research, USA), a constant voltage of −0.05 V was applied until a total charge of 1.5 C·cm$^{-2}$ had flow. A mixture solution of 40 g/l $KAu(CN)_2$ and 100 g/l $KH_2PO_4$ was loaded in the AAO, and constant voltage of −1.0 V was applied, thereby electroplating gold into the pores of the AAO nanopores.

During electroplating, the Cu/AAO electrode was used as a working electrode, a platinum plate provided the counter electrode, and Ag/AgCl (KCl saturated solution) was used as a reference electrode.

(iii) Removal of Copper and AAO

The Au/Cu/AAO plated filter thus obtained was immersed in a 6 M $HNO_3$ aqueous solution for 3 hours to remove copper, and washed with DI water, and the Au/AAO was then immersed in a 3 M NaOH aqueous solution for 3 hours or longer, to dissolve and remove the AAO. The nano-gold rods (which had been deposited in the pores of the AAO filter) thus obtained was washed with deionized ("DI") water.

Figure 2:
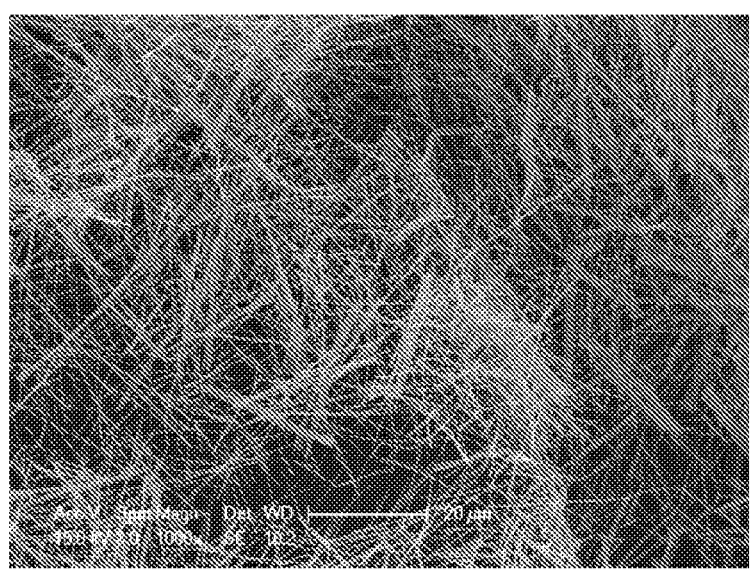
FIG. 2 is a scanning electron micrograph of an exemplary nano-metal rod, obtained in the Example.

The diameter of the nano-gold rod was about 250 to about 300 nm, and the length thereof was about 25 to about 30 μm. A scanning electron micrograph ("SEM") showing the resulting nano-gold rods is shown in FIG. 2.

(C) Synthesis of Nano-Metal-Bound Monomer and Conductive Polymer Composite
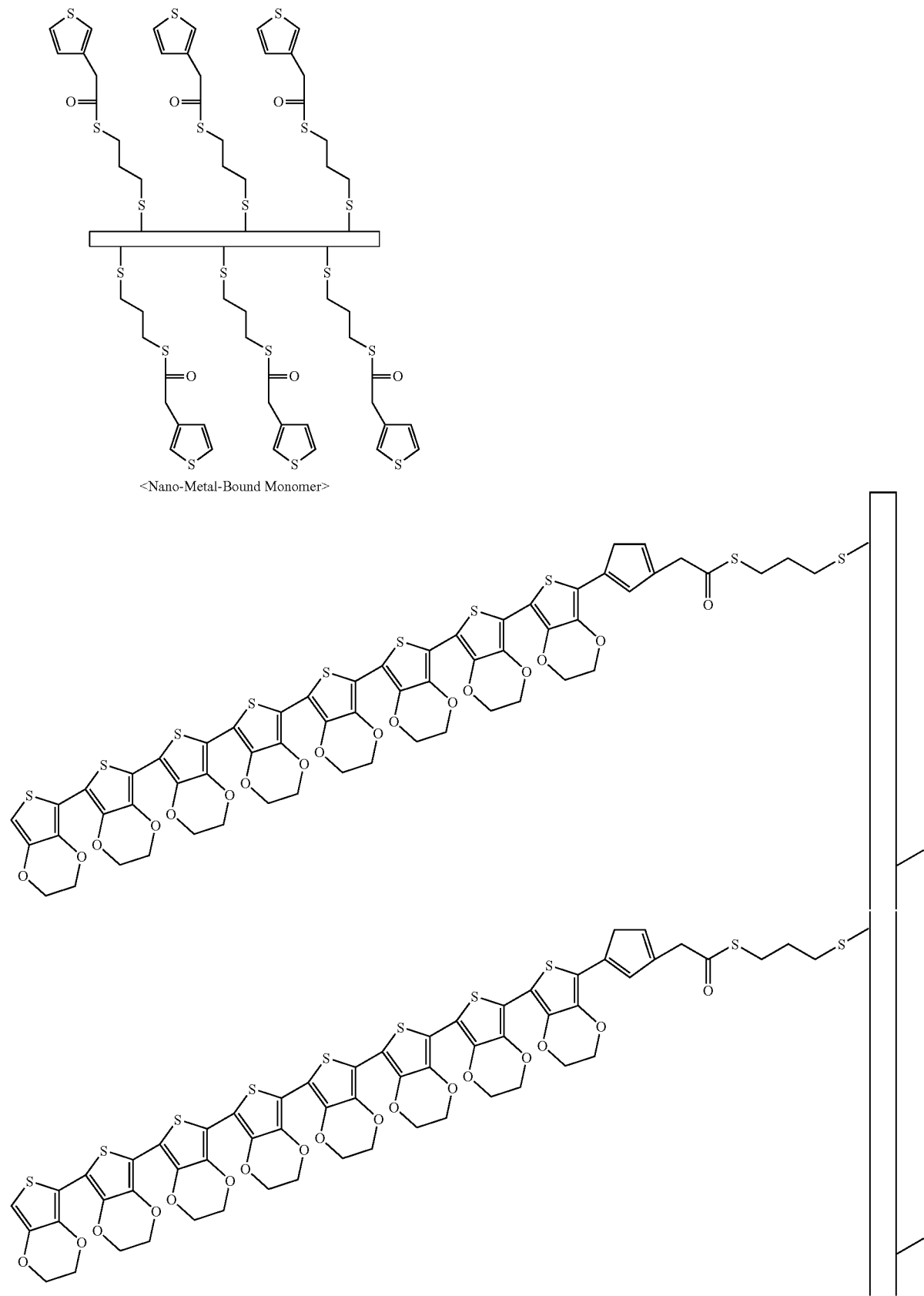

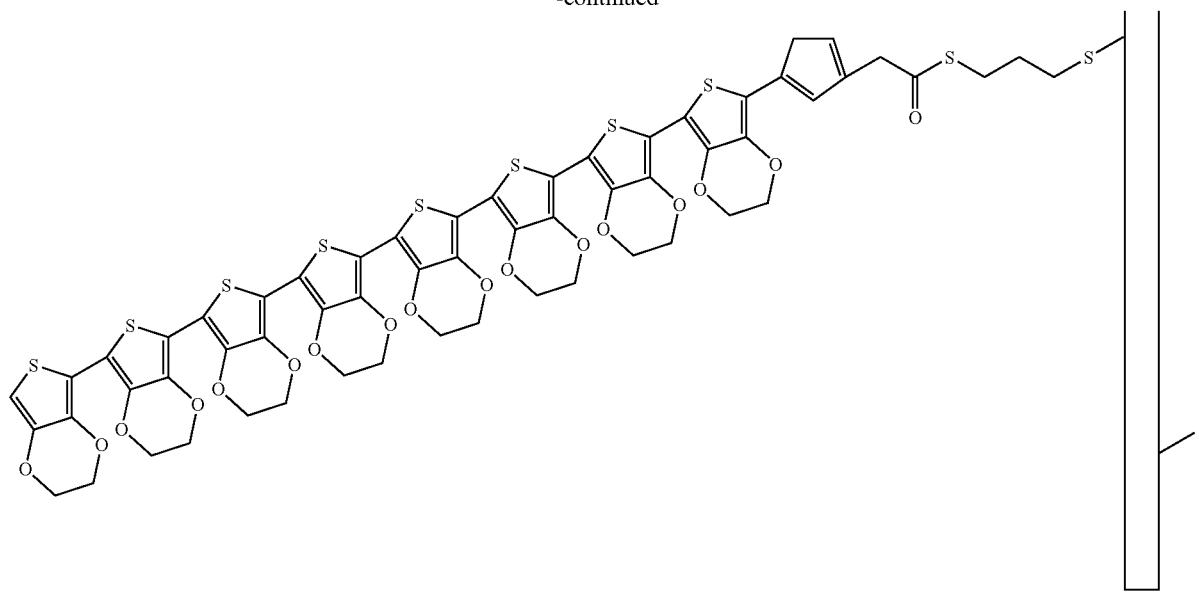
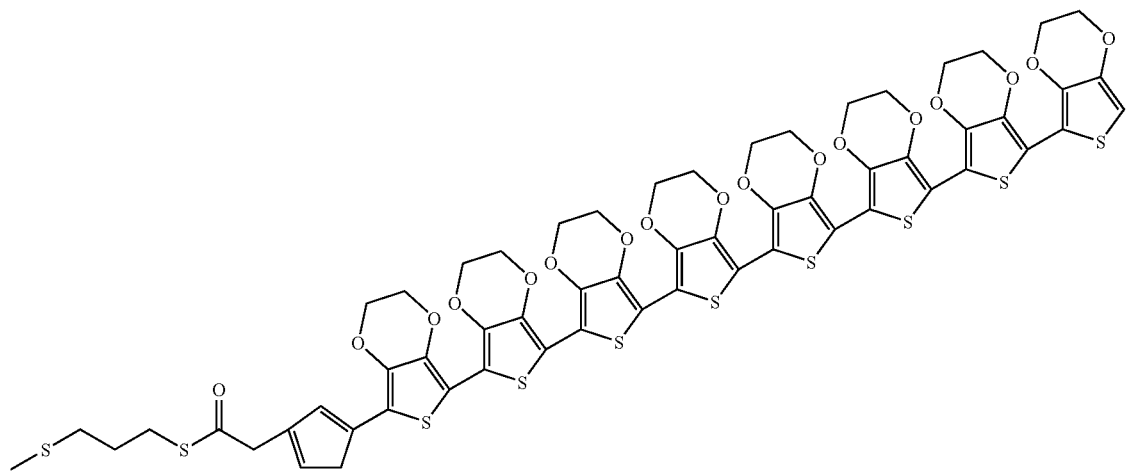
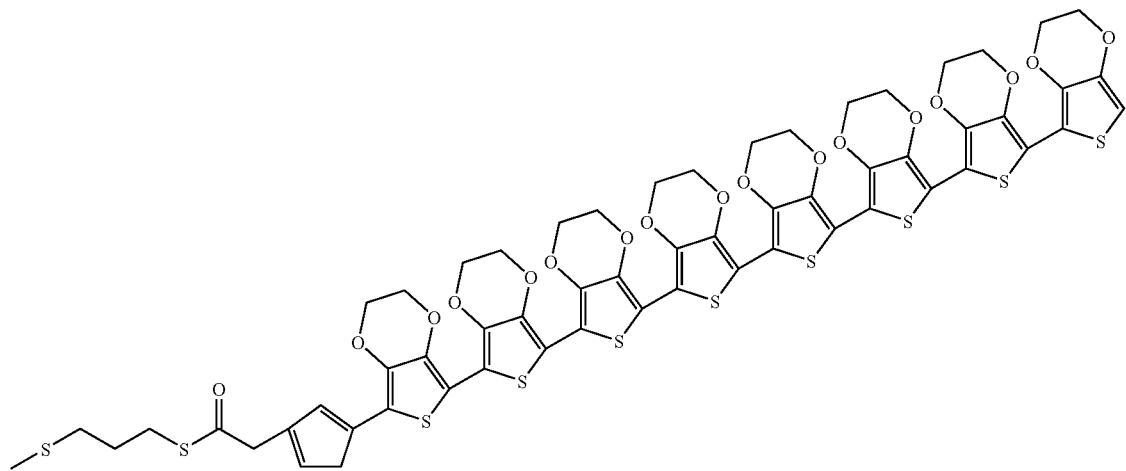

-continued

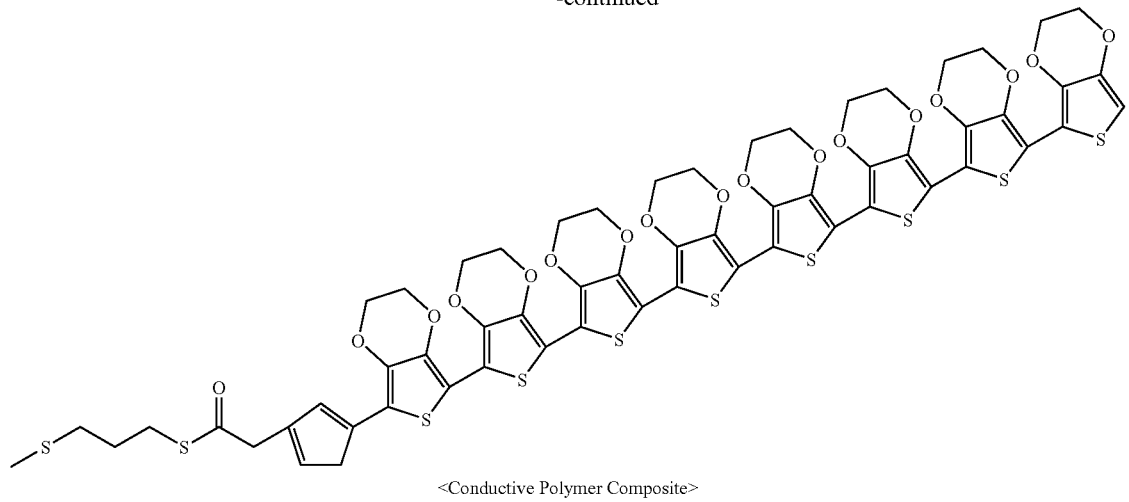

<Conductive Polymer Composite>

As an initiator of poly(3,4-ethylendioxythiophene) ("PEDOT"), which is a conductive polymer, ferric (III) p-toluene sulfonate ("FTS") was used as an initiator, and the molar ratio of the 3,4-ethylenedioxythiophene ("EDOT") monomer to the initiator was set to 1:2.33. Using FTS, which is a strong oxidant, the polymerization of EDOT occurred rapidly, even at room temperature. Imidazole was used as a polymerization inhibitor to adjust the polymerization rate and to ensure transparency. The molar ratio of EDOT to imidiazole was set at 1:2. In the reaction, the EDOT and imidazole were first each diluted to 10 wt % with 2-propanol, respectively, and then mixed together. To the mixture solution was added the nano-gold rods, and the resulting mixture solution mixed by sonicating for 30 min. FTS was then added, and mixing continued for an additional 30 min. The mixture solution was dropped onto a polyethylene terephthalate ("PET") film substrate, and was then uniformly applied over the surface of the substrate using a spin coater. The coated substrate was polymerized at 120° C. for 1 hour, washed with ethanol, and dried, to thereby obtain a nano-gold rod/PEDOT composite film.

To confirm the bond between the nano-gold rod and the monomer, the nano-gold rod before reaction and the nano-metal-bound monomer after reaction were each measured for voltage-current relation by cyclic voltametry ("CV") to determine the individual oxidation-reduction potentials. The results are shown in FIGS. 3 and 4.

Figure 3:
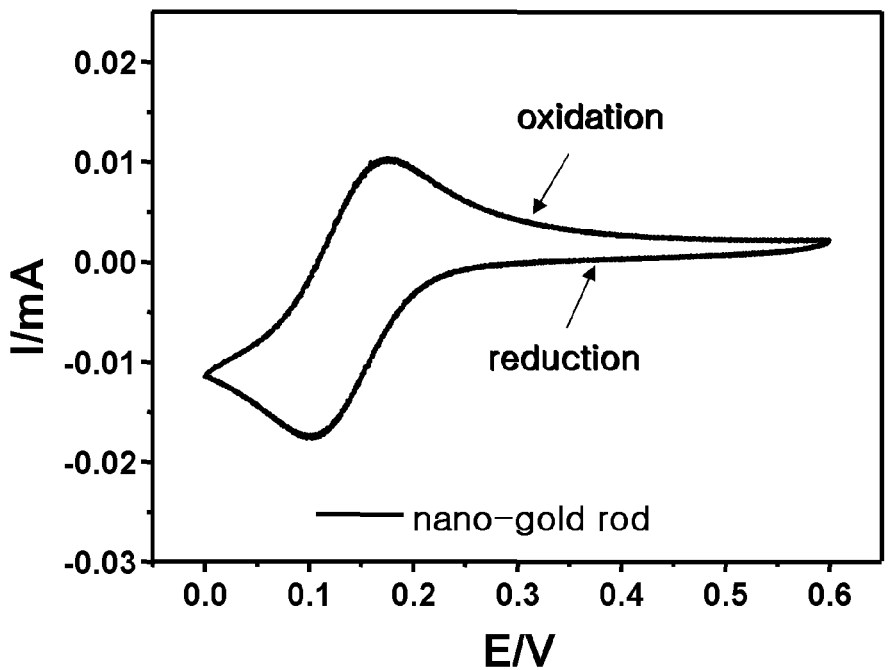
FIG. 3 is a voltage-current graph of the exemplary nano-metal rod, obtained in the Example.
Figure 4:
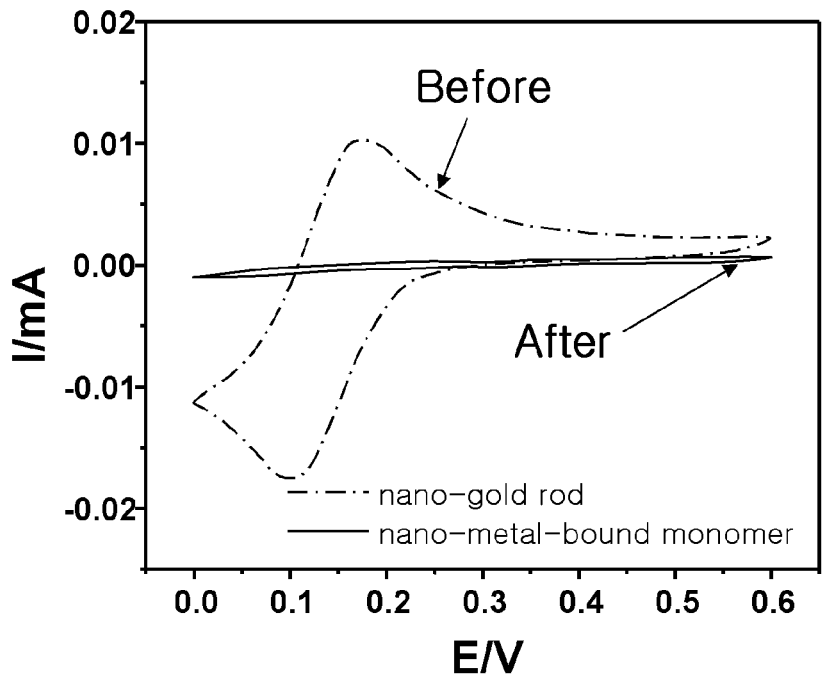
FIG. 4 is a voltage-current graph of an exemplary nano-metal-bound monomer, obtained in the Example.

With reference to FIGS. 3 and 4, in the nano-gold rod before reaction (FIG. 3), oxidation and reduction states were separate, but in the nano-metal-bound monomer after reaction (FIG. 4, "After"), oxidation and reduction states could be seen to disappear. The, the monomer was thereby confirmed to have been bound to the nano-gold rod (which acts as the predominant conductor in the solution) to thus constitute the surface thereof.

Evaluation of Properties

The conductivity, sheet resistance, and light transmittance of the conductive polymer composite including the nano-gold rod obtained in Example were measured. For comparison, a PEDOT (Poly(3,4-ethylenedioxythiophene)) thin film was used, which was prepared by dropping a mixture solution of EDOT and FTS in a molar ratio of 1:2.33 on a PET film substrate, uniformly applying it on the substrate using a spin coater, polymerizing the coated substrate at 120° C. for 1 hour, washing the substrate using ethanol, and drying it.

Experimental Example 1

Measurement of Conductivity and Sheet Resistance

The conductive polymer composite (D) including the nano-gold rod obtained in Example and the comparative conductive polymer were measured for conductivity using a van der Pauw 4-point probe method, and the conductivity measured was used to calculate sheet resistance. The results are shown in Table 1 below.

Experimental Example 2

Measurement of Light Transmittance

The conductive polymer composite (D) including the nano-gold rod obtained in Example and the comparative conductive polymer were measured for light transmittance at 550 nm using a UV-vis spectrophotometer. The results are shown in Table 1 and FIG. 5.

TABLE 1

|  | Conductivity (S/cm) | Sheet Resistance (Ω/square) | Light Transmittance (%) |
|---|---|---|---|
| Example | 800 | 100 | 85 |
| C. Example | 350 | 400 | 85 |

Figure 5:
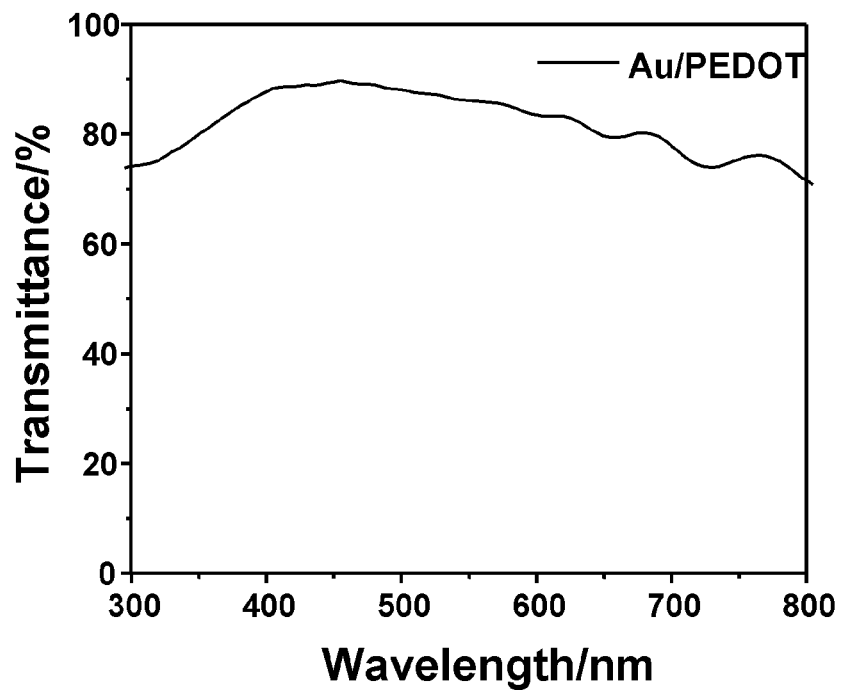
FIG. 5 is a graph of light transmittance of an exemplary conductive polymer composite, synthesized in the Example.

As is apparent from Table 1 and FIG. 5, the conductivity of the conductive polymer composite (D) including the nano-gold rod (Example in Table 1) was determined to be 800 S/cm, which is much higher than that of the PEDOT (C. Example in Table 1). Further, light transmittance was maintained at 80% or higher, and sheet resistance decreased to a level of less than 200 Ω/square. Accordingly, the exemplary conductive polymer composite can substitute for conventional metal electrodes of various devices, unlike conventional conductive polymer material. The exemplary material is a polymer obtained by binding a conductive polymer monomer to metal having high conductivity and then polymerizing the monomer, and is grown in a non-directional form on the metal. Compared to a conventional conductive polymer-conductor mixture form, the exemplary conductive polymer composite exhibits very high conductivity, and thus low sheet resistance. This is believed to occur because the nano-metal conductive polymer composite has a form in which contact resistance with metal is minimized. Further, the metal is present in nano-size, and is dispersed well, thereby preventing a decrease in light transmittance.

Although Exemplary embodiments have been disclosed for illustrative purposes, those skilled in the art will appreciate that various modifications, additions and substitutions are possible, without departing from the scope and spirit of the invention as disclosed in the accompanying claims.

What is claimed is:

1. A conductive polymer composite consisting of a nano-metal rod, wherein a surface of the nano-metal rod is bound with a monomer for binding nano-metal, represented by Formula 1 below, to which conjugated conductive polymer monomers are joined:

Ar-L$_1$-A    [Formula 1]

wherein Ar is thiophenyl, anilinyl, pyrrolyl, furanyl, pyrazolyl, carbazolyl, fluorenyl or derivatives thereof, L$_1$ is a C$_{1~10}$ alkylene group containing one or more hetero atoms selected from the group consisting of S, O, N and Si; a C$_{1~10}$ alkyleneoxy group containing one or more hetero atoms selected from the group consisting of S, O and N; or a C$_{1~10}$ silyleneoxy group containing one or more hetero atoms selected from the group consisting of S, O and N; and A is —SH, —COOH, —SOOH, —CN, —CH$_2$=CH$_2$, —C≡CH, —NH$_2$, or trichlorosilyl.

2. The conductive polymer composite of claim 1, wherein the monomer for binding nano-metal is represented by Formulas 2 to 6 below:

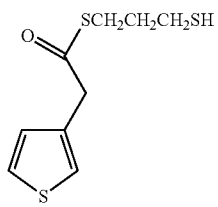
[Formula 2]

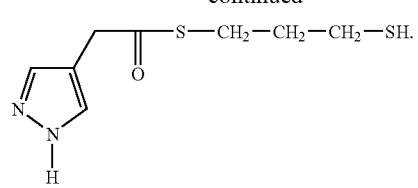
[Formula 3]

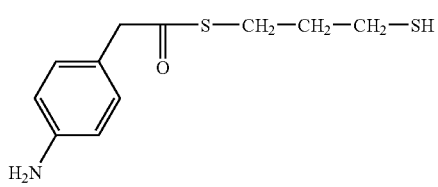
[Formula 4]

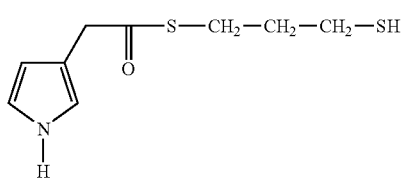
[Formula 5]

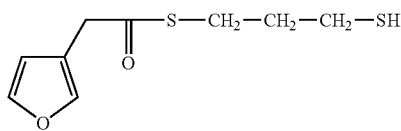
[Formula 6]

3. The conductive polymer composite of claim 1, wherein —SH, —COOH, —SOOH, —CN, —CH$_2$=CH$_2$, —C≡CH, —NH$_2$, or trichlorosilyl, located at an end of the monomer for binding nano-metal, is bound to the surface of the nano-metal rod.

4. The conductive polymer composite of claim 1, wherein the nano-metal is selected from the group consisting of gold, copper, silver, platinum, aluminum, indium, tin, iron, nickel, lead, zinc, mercury, palladium, and alloys thereof.

5. The conductive polymer composite of claim 1, wherein the nano-metal rod has a diameter of from about 1 nm to about 500 nm and a length of from about 1 μm to about 100 μm.

6. The conductive polymer composite of claim 1, wherein the conductive polymer monomer is selected from the group consisting of 3,4-ethylenedioxythiophene, thiophene, aniline, pyrrole, vinylcarbazole, acetylene, pyridine, azulene, indole, phenylacetylene, 1,4-substituted benzene, azine, quinone, phenylmercaptan, furan, isothianaphthene, and derivatives thereof.

7. A method of preparing a conductive polymer composite, comprising:
(a) binding a monomer for binding nano-metal, represented by Formula 1 below, to a surface of a nano-metal rod, thus forming a nano-metal-bound monomer; and
(b) mixing the nano-metal-bound monomer formed in (a), a conductive polymer monomer, a polymerization initiator, and a dopant with a solvent, to obtain a mixture, and then subjecting the mixture to heating and polymerization,
wherein the conductive polymer composite consists of a nano-metal rod, wherein a surface of the nano-metal rod is bound with a monomer for binding nano-metal, represented by Formula 1 below, to which conjugated conductive polymer monomers are joined:

Ar-L$_1$-A    [Formula 1]

wherein Ar is thiophenyl, anilinyl, pyrrolyl, furanyl, pyrazolyl, carbazolyl, fluorenyl or derivatives thereof, L$_1$ is a C$_{1~10}$ alkylene group containing one or more hetero atoms selected from the group consisting of S, O, N and Si; a C$_{1~10}$ alkyleneoxy group containing one or more hetero atoms selected from the group consisting of S, O and N; or a C$_{1~10}$ silyleneoxy group containing one or more hetero atoms selected from the group consisting of S, O and N; and A is —SH, —COOH, —SOOH, —CN, —CH$_2$=CH$_2$, —C≡CH, —NH$_2$, or trichlorosilyl.

8. The method of claim 7, wherein the monomer for binding nano-metal, is represented by Formulas 2 to 6 below:

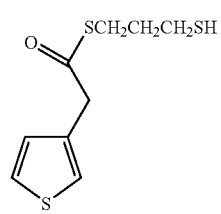
[Formula 2]

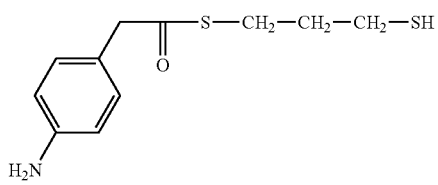
[Formula 3]

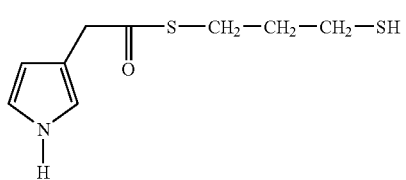
[Formula 4]

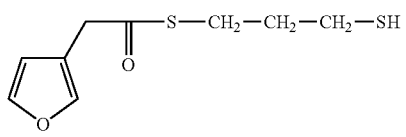
[Formula 5]

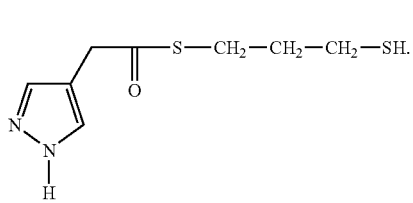
[Formula 6]

9. The method of claim 7, wherein the nano-metal is selected from a group consisting of gold, copper, silver, platinum, aluminum, indium, tin, iron, nickel, lead, zinc, mercury, palladium, and alloys thereof.

10. The method of claim 7, wherein the conductive polymer monomer is selected from a group consisting of 3,4-ethylenedioxythiophene, thiophene, aniline, pyrrole, vinylcarbazole, acetylene, pyridine, azulene, indole, phenylenevinylene, phenylene, azine, quinone, phenylene sulfide, furan, isothianaphthene, and derivatives thereof.

11. The method of claim 7, wherein the (b) further comprises mixing a mixture catalyst.

12. A device comprising the conductive polymer composite of claim 1.

13. A conductive polymer composite comprising a nano-metal rod, wherein a surface of the nano-metal rod is bound with a monomer for binding nano-metal, represented by Formulas 2 to 6 below, to which conjugated conductive polymer monomers are joined:

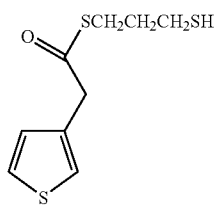
[Formula 2]

14. A method of preparing a conductive polymer composite, comprising:
(a) binding a monomer for binding nano-metal, represented by Formulas 2 to 6 below, to a surface of a nano-metal rod, thus forming a nano-metal-bound monomer; and
(b) mixing the nano-metal-bound monomer formed in (a), a conductive polymer monomer, a polymerization initiator, and a dopant with a solvent, to obtain a mixture, and then subjecting the mixture to heating and polymerization:

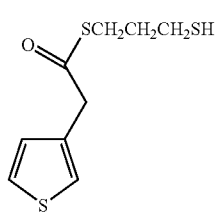
[Formula 2]

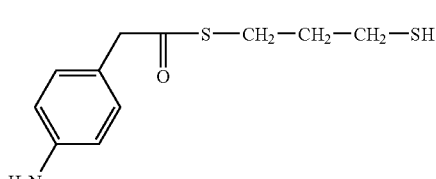
[Formula 3]

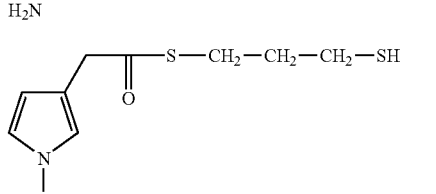
[Formula 4]

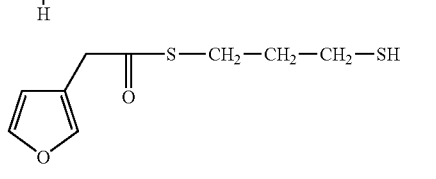
[Formula 5]

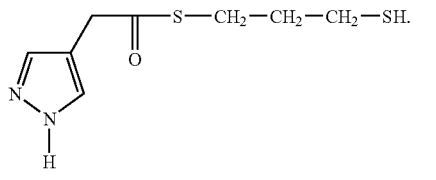
[Formula 6]

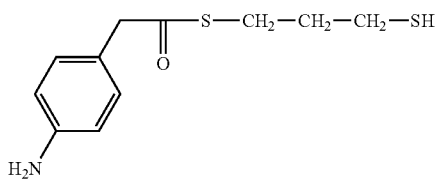
[Formula 3]

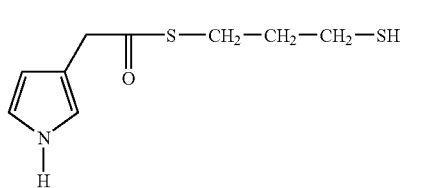
[Formula 4]

-continued
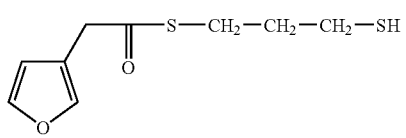
[Formula 5]
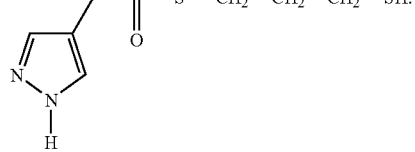
[Formula 6]
* * * * *